(12) United States Patent
Diedrich et al.

(10) Patent No.: US 7,441,443 B2
(45) Date of Patent: Oct. 28, 2008

(54) DRYING BALANCE

(75) Inventors: Karin Diedrich, Hardegsen (DE); Horst Nagel, Seeburg (DE); Wilfried Spannagel, Goettingen (DE)

(73) Assignee: Sartorius AG, Goettingen (DE)

( * ) Notice: Subject to any disclaimer, the term of this patent is extended or adjusted under 35 U.S.C. 154(b) by 0 days.

(21) Appl. No.: 11/797,001

(22) Filed: Apr. 30, 2007

(65) Prior Publication Data
US 2007/0199370 A1  Aug. 30, 2007

Related U.S. Application Data

(63) Continuation of application No. PCT/EP2005/010160, filed on Sep. 21, 2005.

(30) Foreign Application Priority Data
Nov. 6, 2004  (DE) .................. 10 2004 053 734

(51) Int. Cl.
G01N 5/02  (2006.01)
G01N 25/56  (2006.01)

(52) U.S. Cl. ........................................... 73/73
(58) Field of Classification Search .................. 73/73, 73/75; 177/245, 50; 374/14
See application file for complete search history.

(56) References Cited

U.S. PATENT DOCUMENTS

| | | | | |
|---|---|---|---|---|
| 2,231,035 A * | 2/1941 | Stevens et al. | ............. | 324/667 |
| 2,816,437 A * | 12/1957 | Hornberger et al. | ............. | 73/76 |
| 2,832,215 A * | 4/1958 | Brabender | ............. | 73/76 |
| 3,090,004 A * | 5/1963 | Breen et al. | ............. | 324/669 |
| 3,405,268 A | 10/1968 | Brunton | ............. | 250/339.1 |
| 3,748,473 A * | 7/1973 | Chen | ............. | 250/392 |
| 4,165,633 A * | 8/1979 | Raisanen | ............. | 73/76 |
| 4,354,244 A * | 10/1982 | Miller et al. | ............. | 702/23 |
| 4,466,198 A | 8/1984 | Doll | ............. | 34/257 |
| 4,485,284 A | 11/1984 | Pakulis | ............. | 219/705 |
| 4,750,143 A * | 6/1988 | Heitz et al. | ............. | 73/76 |
| 4,798,252 A * | 1/1989 | Knothe et al. | ............. | 177/245 |
| 4,838,705 A * | 6/1989 | Byers, Jr. et al. | ............. | 374/14 |
| 4,964,734 A * | 10/1990 | Yoshida et al. | ............. | 374/14 |
| 5,046,356 A | 9/1991 | Osaki et al. | ............. | 73/73 |
| 5,293,019 A | 3/1994 | Lee | ............. | 219/708 |
| 5,617,648 A * | 4/1997 | Leisinger et al. | ............. | 34/226 |
| 5,787,600 A * | 8/1998 | Leisinger et al. | ............. | 34/89 |
| 5,983,711 A | 11/1999 | Pappas et al. | ............. | 73/76 |
| 6,227,041 B1 * | 5/2001 | Collins et al. | ............. | 73/76 |

(Continued)

FOREIGN PATENT DOCUMENTS

DE  32 31 004 C2  2/1984

(Continued)

Primary Examiner—Hezron E. Williams
Assistant Examiner—Tamiko D Bellamy
(74) Attorney, Agent, or Firm—Sughrue Mion, PLLC

(57) ABSTRACT

A drying balance (1) including a pan (3) that rests on a weighing system (2) as well as a heat source (5) for heating and drying a sample (4) on the pan. A sensor (11) measures the absorption coefficient, transmission coefficient, or reflection coefficient of the sample (4) in at least one predefined spectral range, or measures the moisture dependent dielectric constant of the sample while the weighing system (2) measures the moisture dependent weight of the sample (4). The drying balance allows the entire calibration curve of the sensor (11) to be determined in a single drying process.

21 Claims, 3 Drawing Sheets

U.S. PATENT DOCUMENTS

| | | | |
|---|---|---|---|
| 6,302,577 B1 * | 10/2001 | Jennings et al. | 374/14 |
| 6,920,781 B2 * | 7/2005 | Olesen | 73/73 |
| 2001/0030543 A1* | 10/2001 | Joshi et al. | 324/643 |
| 2002/0035792 A1* | 3/2002 | Scalese et al. | 34/259 |

FOREIGN PATENT DOCUMENTS

| | | | |
|---|---|---|---|
| DE | 10123101 A1 | * | 11/2002 |
| EP | 0 526 297 A1 | | 2/1993 |
| FR | 2 714 182 A | | 6/1995 |
| GB | 2194340 A | * | 3/1988 |
| JP | 58 018155 A | | 2/1983 |
| JP | 58 165038 A | | 9/1983 |
| WO | WO 00/14552 A1 | | 3/2000 |

* cited by examiner

DRYING BALANCE

This is a Continuation of International Application PCT/EP2005/010160, with an international filing date of Sep. 21, 2005, which was published under PCT Article 21(2) in German, and the disclosure of which is incorporated into this application by reference.

FIELD AND BACKGROUND OF THE INVENTION

The invention relates to a drying balance with a pan which rests on a weighing system and a heat source for heating and drying a sample on the pan. The invention further relates to a method for operating this drying balance.

Conventional drying balances are disclosed for example, in German Patents DE 36 15 660 C2 and DE 199 56 372 C2.

Drying balances of this type are relatively fast compared to those using a drying cabinet method. However, it still requires several minutes to determine the moisture content of the sample. In industrial production the moisture content of a material must be determined within no more than a few seconds so as not to slow down the production process. For that purpose, drying balances of this kind are not usable. Instead, indirect measurement methods are frequently used. One example for such an indirect measurement method is the method of measuring optical absorption.

Calibration curves of indirect moisture measuring devices are typically recorded point for point by measuring different samples with different moisture contents. At the same time the indirect moisture measuring device and the known drying balance are separately used to determine the calibration curve on the basis of the value pairs thus obtained. This method requires the production of a plurality of samples and is therefore complicated and time-consuming.

German Utility Model DE 88 02 378 U1 discloses a drying balance with built-in temperature sensor for monitoring and controlling the output of the heat source. A temperature calibration disk with an additional temperature sensor can be connected to the drying balance. By applying a thin layer of the sample material, the temperature calibration disk is given the absorption coefficients of the sample material. In a calibration cycle, the temperature sensor built into the drying balance can be calibrated relative to the additional temperature sensor in the temperature calibration disk. In a subsequent measurement cycle, the calibration curve is used to control the heat source. The actual samples are used in such a way that the specified drying temperature of the sample is met. DE 88 02 378 U1 further provides for the use of an easy-to-handle temperature disk as a secondary standard. The absorption coefficient of the sample material is simulated by strongly and weakly absorbing surfaces in the correct area ratio, wherein a one-time measurement must be used to determine the correct area ratio relative to the temperature calibration disk with the sample substance.

SUMMARY OF THE INVENTION

One object of the invention is to further develop a drying balance of the aforementioned type such that it can be used for a simplified calibration of indirect moisture measuring devices.

According to one aspect of the invention, the sensor measures at least one of a moisture dependent absorption coefficient, transmission coefficient, and reflection coefficient of the sample in at least one predefined spectral range or the moisture dependent dielectric constants of the sample, while the weighing system measures the weight. This is achieved, for instance, by at least partly integrating a sensor into the drying balance in addition to the weighing system for measuring the moisture dependent weight of the sample.

By integrating the sensor for measuring the absorption coefficient, transmission coefficient or reflection coefficient or the dielectric constants into the drying balance, the absorption, transmission or reflection coefficient or the dielectric constant can be measured continuously during the drying process. The weight value of the sample, which is also continuously determined by the weighing system, can be used to calculate the moisture content of the sample at the end of the drying process. This provides value pairs for the moisture content of the sample and the associated absorption coefficient, transmission coefficient or reflection coefficient or the associated dielectric constant after the end of the drying process, which directly give the calibration curve. If this measurement is conducted in accordance with another aspect of the invention and using a sample with maximum moisture content, the entire calibration curve can be determined in a single drying process of the sample.

BRIEF DESCRIPTION OF THE DRAWINGS

The invention will now be described with reference to the diagrammatic figures depicted in the drawing, in which.

DETAILED DESCRIPTION OF THE EXEMPLARY EMBODIMENTS OF THE INVENTION

Figure 1:
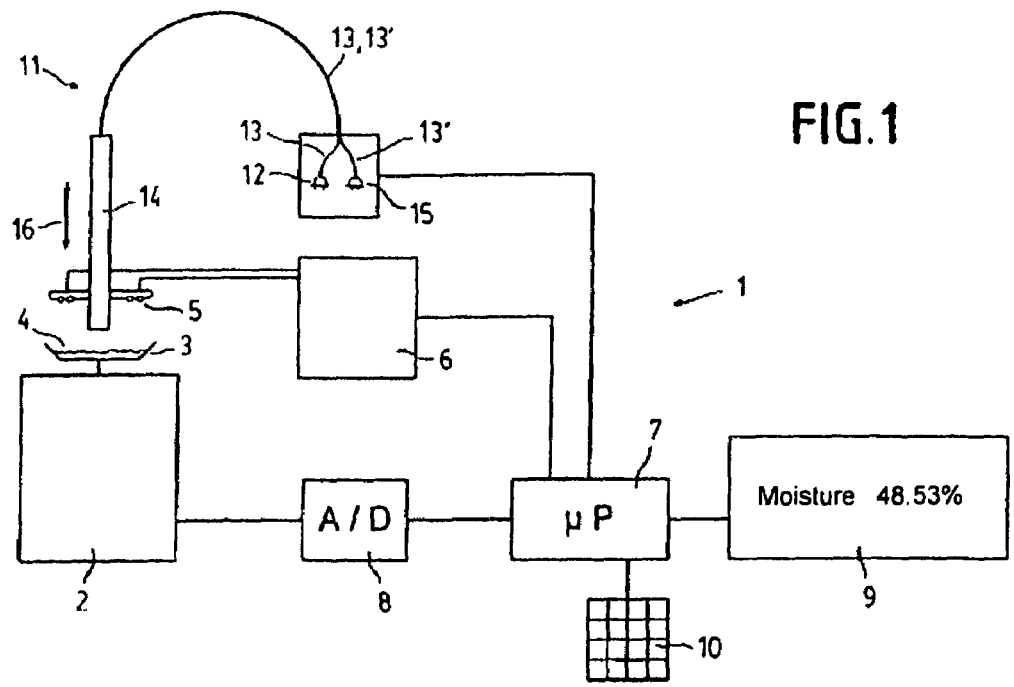
FIG. 1 is a block diagram of an exemplary embodiment of the drying balance.

FIG. 1 is a block diagram illustrating an exemplary embodiment of the drying balance 1. It consists of a weighing system 2 with a pan 3 that carries a sample 4 which is to be dried and the moisture content of which is to be measured. The indicated heat source 5 for heating and drying the sample is an annular radiant heater, but any other conventional heat sources may also be used. The output of the heat source 5 is controlled by an electronic control system 6. The desired heat output is predefined by a central electronic unit 7. The output signal of the weighing system 2—i.e., the instantaneous mass of the sample 4—is digitized by an analog-to-digital converter 8 and supplied to the central electronic unit. During the drying process, it is possible to display on a display 9 the instantaneous mass of the sample as a ratio of the initial mass of said sample.

After the drying process is concluded, the determined moisture content is displayed. To operate the drying balance, a keyboard 10 is used. The parts of the drying balance 1 described above, their construction and their function are generally known. Consequently, there is no need to describe them in detail. A detailed description may be found, for example, in the cited documents DE 36 15 660 C2 and DE 199 56 372 C2, which are incorporated into the present application by reference.

The additional sensor 11 for measuring the absorption coefficient, transmission coefficient or reflection coefficient of the sample 4 is incorporated into the drying balance 1. The absorption, transmission or reflection coefficient is, for example, measured in the near infrared. In the exemplary embodiment depicted, the sensor 11 consists of a radiation source 12 in the form of an infrared LED and one or more optical waveguide(s) 13 which transmit(s) the radiation of the radiation source 12 to the sample. The end of the optical waveguide 13 on the side of the sample is fixed within a tubular end piece 14. The sample 4 is thus illuminated by the infrared light of the radiation source 12. The light reflected by the sample is captured by one or more optical waveguides 13', the ends of which are likewise fixed in the end piece 14, and is transmitted to a radiation detector 15 in the form of an infrared photo element. The infrared spectral range in which the reflection measurement occurs is determined by the radiation source (narrow-band radiation source and broad-band radiation detector) or by the radiation detector (broad-band radiation source and narrow-band radiation detector) or by interposed filters (broad-band radiation source and broad-band radiation detector and interposed narrow-band filter). Even the optical waveguides 13, 13' themselves can act as narrow-band filters if they are formed of a corresponding type of glass.

It is also possible to use a spectrometer with a position-sensitive photo detector connected downstream as a filter element determining the spectral range. In this exemplary embodiment the predefined spectral range can be varied by analyzing different ranges of the position-sensitive photo detector. As a result, two different spectral ranges for measurement or a shifting of the used spectral ranges as a function of the temperature of the sample 4 can be used directly and consecutively. The shifting of the spectral range can be controlled through software by the central electronic unit 7.

The dependence of the reflection coefficients on the moisture content of the sample is particularly significant, e.g., in the wavelength range around 1.4 μm and in the wavelength range around 1.9 μm, so that these spectral ranges are preferred.

In the aforesaid it has been assumed that the infrared light reflected on the surface of the sample 4 and thus the reflection coefficient of the sample material is measured. This is accurate for strongly absorbing sample materials where the penetration depth of the radiation is low. There are also materials, however, which absorb the radiation only weakly in the defined spectral range. For these materials, the penetration depth of the radiation is greater than the layer thickness of the sample 4. If the pan 3 is given a strongly reflective (=specular) surface, the non-absorbed portion of the radiation is also returned to the waveguides (13') and is measured. In this case, the superposition of the reflection coefficient and the transmission coefficient can be measured in the geometry according to FIG. 1 for a given layer thickness. To measure the pure transmission coefficient a geometry is required in which the radiation detector (or the end of the associated waveguides) is arranged below the (radiation-permeable) pan with the sample. The absorption coefficient is usually determined indirectly using the well-known mathematical interdependence of absorption coefficient, transmission coefficient and reflection coefficient.

FIG. 1 further indicates by arrow 16 that the end piece 14 of the waveguides is vertically displaceable. As a result, the end piece 14 can be located closely above the surface of the sample 4 as the absorption coefficient, transmission coefficient or reflection coefficient is measured to obtain a good radiation yield for the radiation detector. Between separate measurements, the end piece 14 may be located higher to avoid shielding the sample from the radiation of the heat source 5, which would affect the uniformity in the heating of the sample.

In FIG. 1, the end piece 14 is depicted in a central position. In the measurement of the transmission coefficient, where what matters is a predefined layer thickness of the sample, it is also feasible to use the lower end position of the end piece 14 to adjust the predetermined layer thickness.

If the heat source 5 is a radiant heater that emits (heat) radiation in the same spectral range in which the (measurement) radiation source 12 emits (measurement) radiation, interference-free measurement can be achieved through conventional clock-pulse operation of the (measurement) radiation source 12 (chopper operation).

If the measured value for the absorption coefficient, transmission coefficient or reflection coefficient is to be measured as an average across a relatively large area of the sample 4, this can be readily achieved by a rotatable pan with a rotary drive and a slightly eccentric arrangement of the end piece 14.

Figure 2:
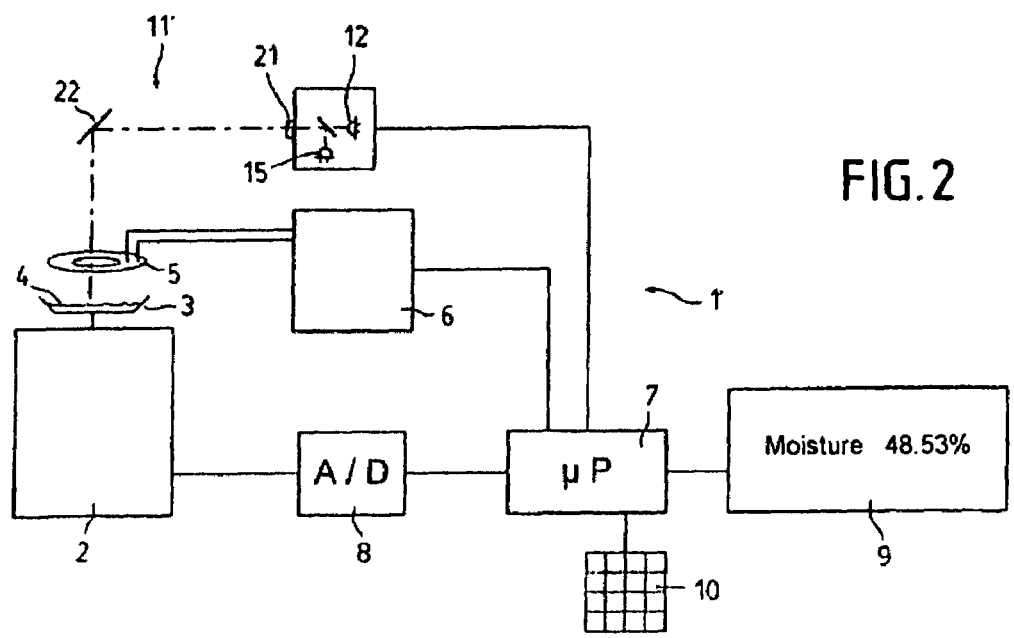
FIG. 2 is a block diagram of another exemplary embodiment of the drying balance.

FIG. 2 is a block diagram illustrating another exemplary embodiment of the drying balance. Components identical or analogous to those of FIG. 1 are identified by the same reference numerals and will not be described anew here.

The drying balance 1' depicted in FIG. 2 uses free space optics instead of waveguide optics. Accordingly, the sensor 11' for measuring the absorption coefficient, transmission coefficient or reflection coefficient consists of the radiation source 12, focusing optics 21 and a deflection mirror 22. This causes the radiation of the radiation source 12 to be focused onto the surface of the sample 4 and the radiation reflected by the surface of the sample to be focused correspondingly onto the radiation detector 15. The focusing optics 21 are of course indicated only schematically. For example, the deflection mirror 22 could also be concave and assume the focusing function. These free space optics illustrated in FIG. 2 work much like the waveguide optics depicted in FIG. 1 and allow all the same variants discussed with reference to FIG. 1.

Figure 3:
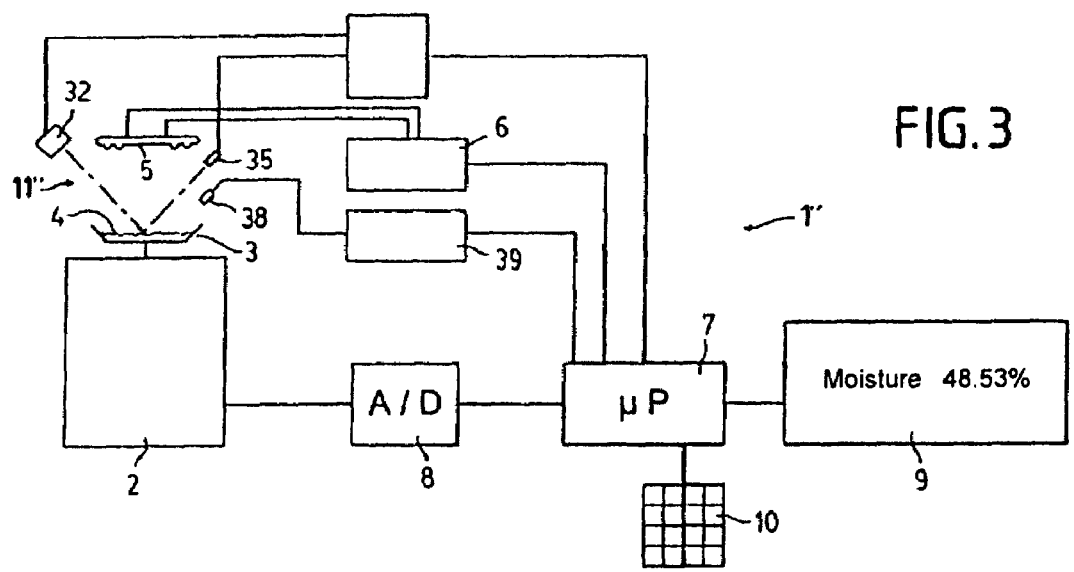
FIG. 3 is a block diagram of a third exemplary embodiment of the drying balance.

FIG. 3 is a block diagram illustrating a third exemplary embodiment of the drying balance. This embodiment is similar to that depicted in FIG. 2. Components identical or analogous to those of FIG. 2 are identified by the same reference numerals and will not be described anew here. In the drying balance 1" shown in FIG. 3, the radiation source 32 and the radiation detector 35 of sensor 11 are arranged separately and irradiate the sample 4 at a 45° angle and measure the reflected infrared light also at a 45° angle. Otherwise they operate in the same manner as the embodiments depicted in FIGS. 1 and 2.

FIG. 3 further shows a sensor 38 for measuring the temperature of the sample 4. This sensor can operate contactlessly, for example. The signal of the sensor 38 is analyzed in the associated electronic analysis unit 39 and is supplied to the central electronic unit 7. The central electronic unit can then make temperature corrections, if necessary, to correct temperature dependencies of individual sensors or a temperature dependency of the absorption coefficient, transmission coefficient or reflection coefficient.

Figure 4:
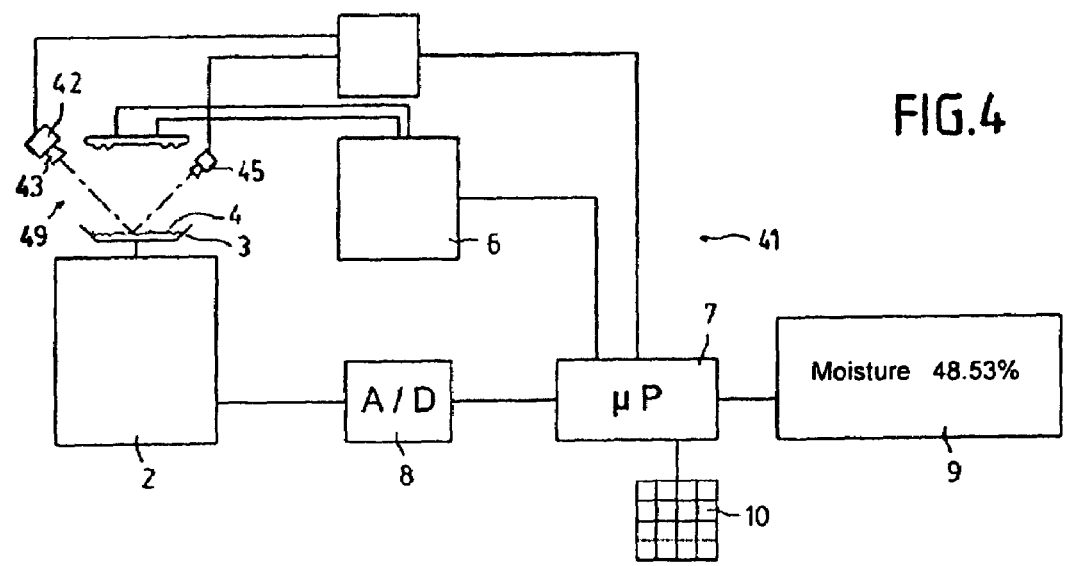
FIG. 4 is a block diagram of a fourth exemplary embodiment of the drying balance.

The exemplary embodiments illustrated in FIGS. 1 to 3 all work in the infrared spectral range. It is also possible to use any other spectral range. FIG. 4 shows a fourth exemplary embodiment of the drying balance in which the sensor 49 is designed for the microwave spectral range. Components identical or analogous to those shown in FIG. 1 to 3 are again identified by the same reference numerals and are not described anew here. The radiation source 42 of the drying balance 41 depicted in FIG. 4 is a microwave klystron with an upstream horn radiator 43 for emitting the microwave radiation onto the sample 4. A microwave antenna acting as the radiation detector 45 detects the reflected microwave radiation. For the rest, the mode of operation of this unit is identical or analogous to that of the above-described exemplary embodiments.

In the exemplary embodiment shown in FIG. 4 the microwave radiation source 42 is equipped with sufficient transmission power that this microwave radiation source will simultaneously serve as the heat source. The separate heat source 5 is eliminated in this case. Microwave radiation is absorbed, in particular, by water molecules and is therefore a very effective heat source for moist samples.

In the exemplary embodiments illustrated in FIGS. 1 to 3 it is also possible to use a microwave heat source to heat and dry the sample and to measure the absorption coefficient, transmission coefficient or reflection coefficients in the infrared spectral range.

Figure 5:
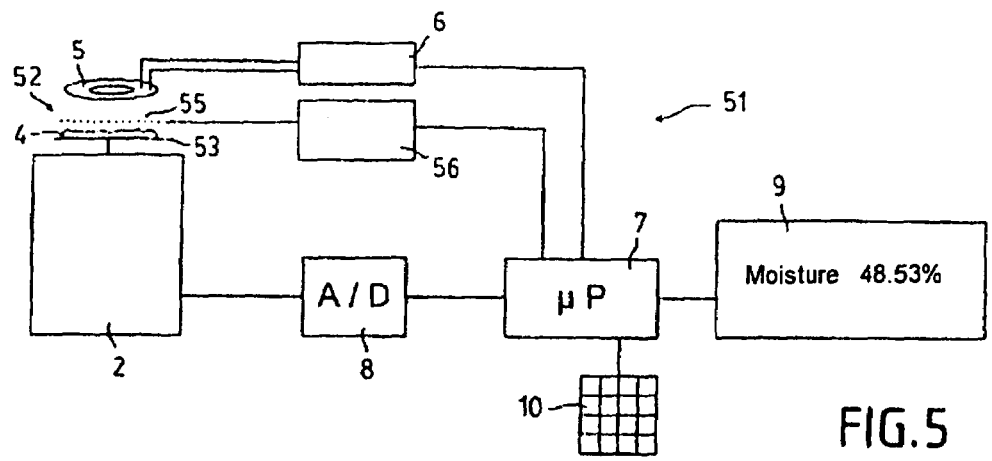
FIG. 5 is a block diagram of a fifth exemplary embodiment of the drying balance.

FIG. 5 shows a fifth exemplary embodiment of the drying balance. Components identical or analogous to those depicted in FIGS. 1 to 4 are again identified by the same reference numerals and are not explained anew here. The drying balance 51 has a built-in sensor 52 for measuring the dielectric constants. The sensor 52 consists of a metal wire mesh as the electrode 55 which is arranged above and parallel to the pan 53. Together with the grounded metal pan 53, the wire mesh of the electrode 55 forms a capacitor for measuring the dielectric constants of the sample 4. The associated electronic capacity measurement unit 56 is indicated only schematically since such units are known to those skilled in the art.

When using the drying balance according to one of the described exemplary embodiments of the invention, it is preferred to use a sample 4 with a maximum moisture content. At short intervals during the drying process, the signal of the sensor 11, 11', 11", 49 or 52 is recorded and stored in the central electronic unit 7. At or about the same time, the instantaneous weight of the sample is recorded by the weighing system 2 and is also stored in the central electronic unit 7. As a result, value pairs for the sensor signal and the sample weight are established in the central electronic unit 7.

After the drying process is concluded and the dry weight is known, the respective intermediate sample weights can be converted to moisture contents (or to absolutely dry values). The value pairs, which can then be calculated for the sensor signal and the associated moisture content, directly give the individual points of the calibration curve for the sensor. Thus, a single drying process can be used to determine the complete calibration curve of the respective sensor for the respective sample type.

Figure 6:
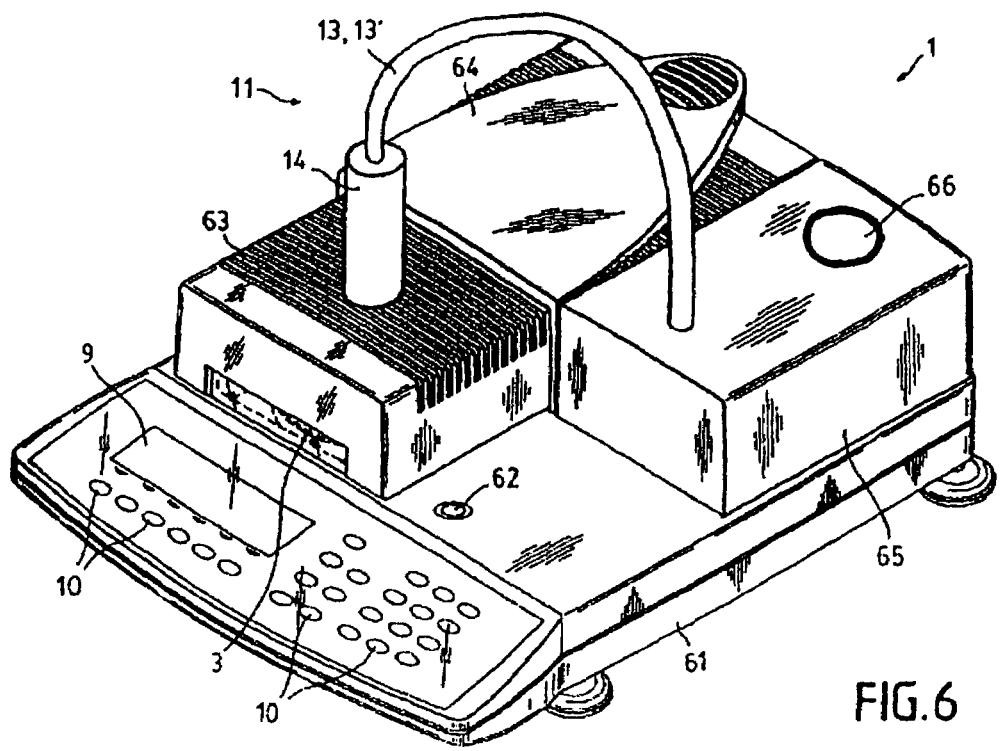
FIG. 6 is a perspective view of the exemplary embodiment of the drying balance shown in FIG. 1.

The schematic block diagrams shown in FIGS. 1 to 5 are intended to explain and illustrate the functioning of the system. FIG. 6 depicts an example of an actual device in a perspective view. This device works with glass fiber optics in the infrared spectral range, i.e., in accordance with the block diagram of FIG. 1. Components identical or analogous to those of FIG. 1 are identified by the same reference numerals, even though they are depicted differently in FIG. 6.

The components of the drying balance 1 visible in FIG. 6 include a housing 61, the display 9, the operating keyboard 10 and a vial 62. Only a small portion of the pan 3 is visible underneath the housing section 63. To load the pan, the displaceable housing section 63 can be shifted rearwardly underneath the housing section 64. The heat source for heating the sample is fixed directly under the top wall of the displaceable housing section 63 and is displaced together with the latter. Only the end piece 14 and the waveguides 13, 13' of the sensor 11 for measuring the absorption coefficient, transmission coefficient or reflection coefficient of the sample, are visible.

The radiation source and the radiation detector are accommodated inside (integrated in) the housing section 65 and are therefore not visible. The end piece 14 can be fixed at two different heights: in a lower measuring position and a slightly higher standby position, as explained above with reference to FIG. 1.

After the drying and calibration process is concluded, the end piece 14 can be removed from the opening in the displaceable housing section 63 and placed into an opening 66 (park position). The displaceable housing section 63 can then be shifted rearwardly to make the pan 3 freely accessible to change the sample. The heat source is switched on and off synchronously with the retraction or extension of the displaceable housing section 63.

The above description of the preferred embodiments has been given by way of example. From the disclosure given, those skilled in the art will not only understand the present invention and its attendant advantages, but will also find apparent various changes and modifications to the structures and methods disclosed. It is sought, therefore, to cover all such changes and modifications as fall within the spirit and scope of the invention, as defined by the appended claims, and equivalents thereof.

What is claimed is:

1. An apparatus comprising:
   a pan;
   a weighing system supporting the pan and measuring the moisture dependent weight of a sample on the pan;
   a heat source heating and drying the sample ; and
   a sensor measuring at least one of a moisture dependent absorption coefficient, transmission coefficient, and reflection coefficient of the sample in at least a predefined spectral range or moisture dependent dielectric constants of the sample, while the weighing system measures the weight,
   wherein the sensor for measuring at least one of the absorption coefficient, transmission coefficient and reflection coefficient consists of a radiation source that irradiates the sample with electromagnetic radiation comprising at least the predefined spectral range and a radiation detector that detects the radiation reflected or transmitted by the sample in the predefined spectral range,
   the apparatus further comprisin a processor, and wherein the sensor comprises a spectrometer and the predefined spectral range is defined by software of the processor.

2. The apparatus as claimed in claim 1, wherein the sensor is partly integrated in the apparatus.

3. The apparatus as claimed in claim 1, wherein the spectral range comprises a wavelength range around 1.4 μm.

4. The apparatus as claimed in claim 1, wherein the spectral range comprises a wavelength range around 1.9 μm.

5. The apparatus as claimed in claim 1, wherein the spectral range comprises a frequency range around 2.45 GHz.

6. The apparatus as claimed in claim 1, wherein the predefined spectral range is defined by filter elements positioned in the radiation path.

7. The apparatus as claimed in claim 1, wherein the predefined spectral range is defined by the radiation source.

8. The apparatus as claimed in claim 1, wherein the predefined spectral range is defined by the radiation detector.

9. The apparatus as claimed in claim 1, wherein the predefined spectral range is defined as a function of temperature.

10. An apparatus comprising:
    a pan;
    a weighing system supporting the pan and measuring the moisture dependent weight of a sample on the pan;
    a heat source heating and drying the sample; and a sensor measuring at least one of a moisture dependent absorption coefficient, transmission coefficient, and reflection coefficient of the sample in at least a predefined spectral range or moisture dependent dielectric constants of the sample, while the weighing system measures the weight, wherein the sensor for measuring at least one of the absorption coefficient, transmission coefficient and reflection coefficient consists of a radiation source that irradiates the sample with electromagnetic radiation comprising at least the predefined spectral range and a radiation detector that detects the radiation reflected or transmitted by the sample in the predefined spectral range, wherein the sensor comprises an optical waveguide coupled to at least one of the radiation source and the radiation detector.

11. The apparatus as claimed in claim 10, wherein an end of the optical waveguide facing the sample is displaceable relative to the sample.

12. The apparatus as claimed in claim 1, wherein at least one of the radiation source and the radiation detector is displaceable relative to the sample.

13. The apparatus as claimed in claim 1, wherein the radiation source is controlled by a clock-pulse.

14. The apparatus as claimed in claim 1, wherein the pan comprising a top side supporting the sample and having a reflective surface in the predefined spectral range.

15. The apparatus as claimed in claim 1, wherein the radiation source is simultaneously the heat source.

16. An apparatus comprising:
a pan;
a weighing system supporting the pan and measuring the moisture dependent weight of a sample on the pan:
a heat source heating and drying the sample ; and
a sensor measuring at least one of a moisture dependent absorption coefficient, transmission coefficient, and reflection coefficient of the sample in at least a predefined spectral range or moisture dependent dielectric constants of the sample, while the weighing system measures the weight, wherein the sensor measuring the dielectric constants of the sample comprises at least one electrode.

17. The apparatus as claimed in claim 1, wherein the pan is mounted for rotation on the weighing system.

18. The apparatus as claimed in claim 1, further comprising a sensor measuring the temperature of the sample; and an electronic unit with analysis algorithms, which correct the data of the sensor measuring at least one of the absorption coefficient, transmission coefficient or reflection coefficient of the sample.

19. The apparatus as claimed in claim 1, further comprising a sensor measuring the temperature of the sample; and an electronic unit with analysis algorithms, which correct the data of the sensor measuring the dielectric constants of the sample as a function of the temperature.

20. A method for operating the apparatus as claimed in claim 1, wherein a sample with a maximum moisture content is used, and wherein, during the drying process, a plurality of value pairs for at least one of the moisture dependent absorption coefficient, transmission coefficient or reflection coefficient or the moisture dependent dielectric constant and for the associated sample weight are recorded for the sample.

21. A method, comprising:

measuring the moisture dependent weight of a sample that rests on a pan of a weighing system;

heating and drying the sample; and measuring, via a sensor, at least one of a moisture dependent absorption coefficient, transmission coefficient, and reflection coefficient of the sample in at least a predefined spectral range or moisture dependent dielectric constants of the sample, while measuring the moisture dependent weight of the sample, wherein the sensor measuring the dielectric constants of the sample comprises at least one electrode.

* * * * *